United States Patent
Reiderman et al.

(10) Patent No.: US 6,278,891 B1
(45) Date of Patent: Aug. 21, 2001

(54) NUCLEAR MAGNETIC RESONANCE METHOD AND APPARATUS FOR BONE ANALYSIS AND IMAGING

(75) Inventors: Arcady Reiderman; Gersh Zvi Taicher, both of Houston, TX (US)

(73) Assignee: Echo Medical Systems, LLC, Houston, TX (US)

( * ) Notice: Subject to any disclaimer, the term of this patent is extended or adjusted under 35 U.S.C. 154(b) by 0 days.

(21) Appl. No.: 09/382,877

(22) Filed: Aug. 25, 1999

(51) Int. Cl.$^7$ ............................................. A61B 5/05
(52) U.S. Cl. ................................. 600/410; 324/309
(58) Field of Search ............................. 324/309; 600/410

(56) References Cited

U.S. PATENT DOCUMENTS

| | | |
|---|---|---|
| 4,442,404 | 4/1984 | Bergmann . |
| 4,510,450 | 4/1985 | Brown . |
| 4,635,643 | 1/1987 | Brown . |
| 4,701,705 | 10/1987 | Rollwitz . |
| 4,850,372 | 7/1989 | Ko et al. . |
| 4,880,007 | 11/1989 | Sadler et al. . |
| 5,126,674 | 6/1992 | Miller et al. . |
| 5,247,934 | 9/1993 | Wehrli et al. . |
| 5,270,651 | 12/1993 | Wehrli . |
| 5,539,309 | 7/1996 | Van Wyk et al. . |
| 5,593,659 | 1/1997 | Winchell et al. . |
| 5,596,274 | 1/1997 | Sezginer . |
| 5,672,968 | 9/1997 | Miller et al. . |
| 5,739,688 | 4/1998 | Krieg . |
| 5,818,228 | 10/1998 | Menon et al. . |
| 5,838,155 | 11/1998 | Bowers . |

OTHER PUBLICATIONS

Kuhn, "NMR Microscopy—Fundamentals, Limits and Possible Applications", Angewandte Chemie, International Edition in English, vol. 29, No. 1, Jan. 1990, pp. 1–19.

Genant et al., "Review—Noninvasive Assessment of Bone Mineral and Structure: State of the Art", Journal of Bone and Mineral Research, vol. 11, No. 6, 1996.

Majumdar et al., "A Review of the Recent Advances in Magnetic Resonance Imaging in the Assessment of Osteoporosis", Osteoporosis International (1995), 5:79–92.

Brochure from Bone Measurement Institute entitled "An Overview of Bone Mass Measurement Technology", no date printed.

(List continued on next page.)

*Primary Examiner*—Christine Oda
*Assistant Examiner*—Dixomara Vargas
(74) *Attorney, Agent, or Firm*—Rosenthal & Osha LLP (57) ABSTRACT

A method for analyzing a bone is disclosed. The method includes measuring nuclear magnetic resonance signals corresponding to an amount of hydrogen nuclei from within a selected portion of the bone. The signals measured includes components corresponding to bound water in the bone. Specific bone tissue volume is determined from an amplitude of the components corresponding to the bound water. In one example, the relaxation times are transverse relaxation times determined from CPMG spin echo amplitudes. In one example, the amplitudes are measured using truncated CPMG sequences having waiting time less than the recovery time of slower relaxing components of the bone being analyzed. In one embodiment, the collagen content of the bone is determined by determining a fluid volume from steady state free precession amplitude of the selected portion. The fluid volume and a bone mineral volume determined from the bound water signal are then subtracted from the total volume of the selected portion to determine the collagen volume. A method for magnetic resonance imaging of a bone is also disclosed, including inducing nuclear magnetic resonance within a selected discrete volume of the bone, determining an amplitude of components in detected NMR signals bound water and repeating bound water amplitude measurements at other selected discrete volumes within the bone to develop an image of the bone.

23 Claims, 6 Drawing Sheets

OTHER PUBLICATIONS

National Osteoporosis Foundation, "First guidelines for osteoporosis issues by National Osteoporosis Foundation in collaboration with multidisciplinary physician organizations", (news release Nov. 5, 1998).

Johnston et al., "Bone density measurement and the management of osteoporosis", Primer on Metabolic Bone Diseases and Disorders of Mineral Metabolism, pp. 93–100 (1996).

NUCLEAR MAGNETIC RESONANCE METHOD AND APPARATUS FOR BONE ANALYSIS AND IMAGING

BACKGROUND OF THE INVENTION

1. Field of the Invention

The invention is related to the field of Nuclear Magnetic Resonance (NMR) and Magnetic Resonance Imaging (MRI) apparatus and methods. More specifically, the invention relates to methods and apparatus for using NMR for rapid, in-vivo determination of bone properties, such as Bone Mineral Density (BMD). The invention more particularly relates to NMR methods and apparatus for diagnosing diseases that affect bone, such as osteoporosis. In addition, the invention relates to methods and techniques of monitoring bone condition during progress of the disease, including the effect of different types of treatments on the disease.

2. Description of the Related Art

The description of the invention and its background are approached in the context of osteoporosis because osteoporosis is recognized as a significant public health problem, and NMR as well as other diagnostic techniques for bone studies have been widely applied and investigated. It is to be explicitly understood that the invention is not limited to the field of study, analysis and monitoring of osteoporosis.

a. Bone in a Human Skeleton

The skeleton serves to support the body, anchor muscles and protect vital organs. The human skeleton consists of approximately 80% of cortical (compact) bone and approximately 20% of trabecular (cancellous, or "spongy") bone. The structure and composition of individual bones varies, and is generally related to the specific function performed by the particular bone. Generally, an anatomical bone consists of about 25% by volume of a specific bone tissue and about 75% by volume of bone marrow. Bone marrow consists of yellow and red bone marrow. Yellow bone marrow includes primarily fat cells (about 85% by volume), water (about 15% by volume) and a small fraction of protein (typically less than about 1% by volume). Red bone marrow mainly includes erythropoetic tissue elements, and its composition is approximately 40% water by volume, 40% fat by volume, and 20% protein by volume. The overall mass of red marrow typically decreases with age. The lost red marrow mass is replaced with yellow marrow. At any age, the proportion of red and yellow marrow varies with the skeletal site. Of the specific bone tissue weight in any particular bone, only about 20% is organic matter (mainly collagen), about 70% is mineralized phase (crystals of hydroxyapatite and amorphous calcium phosphate) and about 10% is water.

In the foregoing discussion and in the description of the invention to follow, these definitions will be used. An "anatomical bone" is a structural, functional part of the skeleton such as the tibia, the radius, the calcaneus, for example. The term "bone" in general refers to a part of any of the previously mentioned anatomical bones, including cross-sections of any anatomical bone. "Bone tissue" is the tissue composition of the cortical bone and trabecular bone making up any anatomical bone. "Specific bone tissue" represents the part of bone tissue excluding any microscopic cavities, blood vessels and the like. The microscopic cavities include osteocytes, lacunae, canliculae, Haversian canals, and Volkmann's canals. "Bone matrix" is the specific bone tissue excluding any chemically bound water. The bound water is also known in the literature as the hydration shell. Bone matrix consists of organic matter, 95 percent of which is in the form of collagen fibers, and inorganic matter referred to as bone mineral. The foregoing definitions have been provided to clarity of the description to follow, because reconciliation of the various terminologies for bones and their components has been difficult since no techniques have been developed to measure the bone matrix quantity in vivo.

Bone continuously undergoes remodeling or turnover during a person's life. Older bone tissue is replaced at anatomically discrete sites with newly formed tissue to avoid cumulative skeletal fatigue damage. Approximately 20% of bone tissue is replaced annually by this process, on a cyclical basis throughout the skeleton. There are five phases to bone remodeling: activation, resorption, reversal, formation and quiescence. The entire remodeling process occurs over approximately 4 to 8 months, with a range of 3 months to 2 years depending on the particular bone.

In bone growth, and during the remodeling process in a normal, healthy person, the organic matter remains a relatively constant fraction of the total specific bone tissue volume, while mineralization of bone occurs by replacement of water by the previously described mineral phase (crystals of bone mineral). Mineralization and crystal growth continue until there is no space left for further mineral expansion. Crystals form and grow within a fixed volume by displacement of water. The space between the crystals become smaller and smaller as the crystals grow, until eventually a state of maximum mineralization is achieved. For bone crystals to grow, mineral ions must diffuse in from fluid circulation. As the intercrystalline spaces become so small as to approach atomic dimensions, ions can no longer diffuse at appreciable rates. Specifically, polyvalent ions of calcium, which form a large part of bone mineral, are large and have high electric charge that prevents them, by electric repulsion, from entering narrow intercrystalline spaces. The same size spaces, however are accessible to univalent ions. Additional chemical evidence suggests that the water in calcified tissues is largely in chemically bound form.

b. Osteoporosis

Osteoporosis is a systematic skeletal disease characterized generally by low bone mass and microarchitectural deterioration of bone tissue, with a consequent increase in susceptibility to fracture. More specifically, in osteoporosis, the volume of the anatomical bones remains unchanged during progress of the disease, but the bones show cortical thickening and porosis, and the bones exhibit a specific bone tissue fraction and a bone mineral fraction of their total volumes which are less than the normal proportions of the anatomical bone volume. However, within the specific bone tissue, the ratio of mineral to organic matter and water remains relatively unchanged. The structural and chemical composition of the specific bone tissue in osteoporotic bone tissue is thus indistinguishable from that of normal bone. This has made analysis of osteoporotic bone difficult using methods known in the art for analyzing bone.

c. Radiologic Bone Densitometry

The National Osteoporosis Foundation has issued specific and aggressive recommendations for managing and preventing osteoporosis in, First guidelines for osteoporosis issues by National Osteoporosis Foundation in collaboration with multidisciplinary physician organizations (news release Nov. 5, 1998). These guidelines include the use of BMD as the single most reliable tool for assessing bone strength and osteoporosis risk. The rationale for using BMD as a monitoring and predictive tool is that there is a well-established relationship between BMD and the ability of bone to withstand compressive, torsional and bending forces. A strong correlation between BMD and the load necessary to induce skeletal failure has been shown, for example, by Johnston and Melton, Bone densitometry measurement and the management of osteoporosis, Primer on Metabolic Bone Diseases and Disorders of Mineral Metabolism, American Society for Bone and Mineral Research, Society Office, pp. 93–100 (1996). In-vivo radiologic bone densitometry methods for diagnosis and therapeutic follow-up include:

I. Conventional skeletal radiography.

This method is relatively insensitive and bone loss is apparent only when bone mass has decreased by about 30–50%.

II. Radiographic photodensitometry.

This method uses exposure to X-rays of a reference wedge alongside the area of interest in measuring the optical density of X-ray films of the bones in the area of interest.

III. Radiogrammetry.

This method relies on an expected linearity of measurements of X-ray films made of cortical bone taken under standardized conditions. The radiogrammetry technique gives values for the cortical width of bone, from which the cortical area of the bone can be derived. This technique is accurate in predicting bone ash weight, but is less sensitive and less specific than absorptiometric measurements, because it does not account for trabecular bone density or cortical bone porosity.

IV. Single Photon Absorptiometry (SPA).

This technique includes measurements related to attenuation by bone and soft tissue of a well-collimated gamma-ray beam. To account for soft tissue absorption, the body part being examined is immersed in a water bath that simulates a uniform soft tissue thickness. Single energy X-ray absorptiometry (SXA) is a related and newly developed technique suitable for scanning appendicular sites. It avoids the need for using specific radioisotopes.

V. Dual-energy Photon Absorptiometry (DPA).

This technique has to be used, for example, to analyze proximal femur and vertebral bodies, which are very irregular bones. The irregularity make delineation of the bones difficult. Furthermore, these bones are surrounded by a widely varying amount of fat, muscle mass and, in the case of the spine, is surrounded by gastrointestinal organs which may be partially filled with gas. These factors limit the use of SPA and SXA. The different thickness of soft tissue can be accommodated by simultaneous measurement of the transmission of gamma ray of two different energies.

VI. Dual-energy X-ray Absorptiometry (DXA).

DXA has now largely replaced DPA because of its greater precision, ease of use and freedom from several technical artifacts. There is no evidence to suggest that DXA has any disadvantages compared with DPA. The theory underlying DPA and DXA requires that there are only two energy absorptive components present, bone and soft tissue, each having uniform composition. In practice, fat has an additional component with attenuation characteristics that differ from those water, muscle and most organs. Fat is distributed non-uniformly in the region of the lumbar spine and may cause errors of up to 10% in estimation of spinal bone mineral mass. Errors can also be introduced by the presence of fat within the vertebral bone marrow.

VII. Quantitative Computed Tomography (OCT).

Under appropriate conditions QCT may provide a measure of volumetric bone mineral density, and cancellous bone can be measured independently of the surrounding cortical bone. The biggest source of error in single X-ray QCT systems is the fat within the bone marrow. Accuracy errors of up to 30% may be introduced from the presence of fat in marrow. The accuracy of QCT may be improved by performing scans at two different X-ray energy levels. Errors of in vivo measurement are much higher than those made in vitro, but the precision of dual-energy QCT can be as high as 10%, much higher than the 2% obtainable with single-energy QCT. A wide range of radiation doses has been used to perform QCT, with values as high as 40 mGy for dual-energy measurement. This comparatively high radiation dose limits the number of repeated measurements that can be done to a single patient, for example, to monitor progression of osteoporosis.

VIII. Photon-scattering Methods and Neutron Activation Analysis.

These techniques have been conceptually and experimentally developed for bone mineral density measurement. However, these techniques were not adequately assessed for screening.

IX. Ultrasound.

Evaluation of bone by ultrasound is based on measurement of velocity, attenuation or reflection of ultrasonic energy imparted to the bone. Interest in these techniques is based on the fact that ultrasonic energy does not introduce ionizing radiation to the body, and may provide some information concerning the structural organization of the bone in addition to information concerning bone mass or density. Ultrasound attenuation measurement has not yet been proven for use as a screening tool. Ultrasound reflection measurement may provide some indication of the material properties of bone but has not been widely studied. Speed of sound has been shown to be a function of both the mass and the modulus of elasticity of the bone, but there have been no studies as yet examining whether or not the speed of sound provides a measure of bone "quality" and a better assessment of bone fragility than bone densitometry alone.

d. Magnetic Resonance Imaging. Particularly of Human Bone

Magnetic Resonance Imaging (MRI) instruments can be used for determining structural properties of a bone. Methods of using MRI measurements for determining the microstructure of a mass of trabecular bone are described, for example, in A Review of Recent Advances in Magnetic Resonance Imaging in the Assessment of Osteoporosis, S. Majumdar. and H. K Genent, Osteoporosis International, Vol. 5, No. 2, pp. 79–92 (1995).

Nuclear Magnetic Resonance (NMR) methods in general are among the most useful nondestructive techniques of material analysis. Particularly, non-invasive examination of a human body by means of NMR is extensive. Specifically, MRI and Magnetic Resonance Spectroscopy (MRS) have many useful application in medical diagnostics. Although Quantitative Magnetic Resonance (QMR) has fewer applications when compared with MRI and MRS, QMR is increasingly being used as a diagnostic tool. In general, NMR/MRI instruments known in the art for analyzing bone typically make measurements corresponding to an amount of time for hydrogen nuclei present in the anatomical bone to substantially realign their spin axes, and consequently their bulk magnetization, with an applied static magnetic field. A superconducting electromagnet, conventional electromagnet or a permanent magnet typically provides the applied static magnetic field. The spin axes of hydrogen nuclei in the bone, in the aggregate, align with the static magnetic field applied by the magnet. Various sequences (selectable length and duration) of radio frequency (RF) magnetic fields are imparted to the bone to momentarily reorient the nuclear magnetic spins of the hydrogen nuclei. RF signals are generated by the hydrogen nuclei as they spin about their axes due to precession of the spin axes. The amplitude, duration and spatial distribution of these RF signals are related to properties of the material which are being investigated by the particular NMR techniques being used.

Conventional MRI can produce an image of the bone, but this image is typically only of the specific bone tissue surface because the number of free (not in chemically bound form) water molecules within the specific bone tissue, and consequently the number of free protons, is very small. It has proven impractical to image the internal structure of bone using MRI techniques known in the art. It is known in the art that bone contains small voids and blood vessels which do contain some free fluid. It is possible using MRI techniques known in the art to develop an image of the bone related to the fluid content of these small fluid-containing voids and vessels within the bone. A particular disadvantage of using conventional MRI techniques to develop such images within the bone, or of the surface of the bone, is the relatively long recovery time between measurements related to the relatively long relaxation time of free protons. It is desirable to be able to develop an image of the internal structure of the bone, and it is even more desirable to be able to develop such an image quickly.

U.S. Pat. No. 4,880,007 issued to Sadler et al and U.S. Pat. No. 5,593,659 issued to Winchell et al describe various methods of improving conventional MRI images using contrast improving agents. It is desirable to have a technique for imaging the internal structure of the bone without the use of such contrast improving agents, for reasons including potential toxicity of such agents, time for the agents to disperse in the body parts to be imaged, and the likelihood that the agent may not disperse sufficiently within the bone to properly image the internal structure thereof.

In the field of in-vivo analysis of bone there have been numerous attempts to use all of the above mentioned Magnetic Resonance methods and techniques. Briefly, these techniques and their limitations are as follows:

I. MRS (Magnetic Resonance Spectroscopy).

U.S. Pat. No. 4,635,643 issued to Brown discloses an MRS method to quantify mineral content of a bone by recording a $^{31}$P spectrum in vivo and comparing it to a MRS spectrum of a reference standard having known concentration of reference minerals. A drawback to this technique is the fact that many human tissue types contain a variety of phosphates which yield $^{31}$P peaks within a very narrow chemical shift range. Thus resolving an individual peak within a $^{31}$P MRS spectrum of measurements made on a bone is very difficult. In addition, MRS requires very high homogeneity and strength of the static magnetic field, due to the required high spectral resolution of chemical shifts, making MRS equipment extremely expensive.

II. MRI (Magnetic Resonance Imaging).

U.S. Pat. No. 5,247,934 issued to Wehrli et al. discloses an MRI method for osteoporosis diagnosis. The essence of the method in the '934 patent is to make an image of the microstructure of trabecular bone, and based on this image and certain empirical criteria, to calculate several trabecular bone parameters such as trabecular thickness, intercept length and fabric tensor. Then, by comparing the obtained set of parameters with data corresponding to a trabecular bone having a known condition, the condition of the bone being examined is then determined. Disadvantages of the method in the '934 patent are first, the typical MRI in-vivo images provide pixel sizes of about 0.5 to 1 millimeters (mm) and section thicknesses of about 2 to 3 mm. This resolution is insufficient to analyze trabecular bone microstructures, which would require image resolution less than the average trabecular thickness, which is about 100 micrometers ($\mu$m). Images with a pixel size of 100×100× 1000 micrometers, as described in the '934 patent, are about the smallest in-vivo pixel sizes which can be attained using the best currently available equipment. This resolution is still not sufficient to resolve trabecular bone microstructures. In addition there are fundamental limitations in MRI physics and technology as explained by Kuhn in, *NMR Microscopy—Fundamentals, Limits and Possible Applications*, ANGEWANDTE CHEMIE, International Edition in English, Vol. 29, No. 1, January 1990, pp. 1–19. The fundamental limitations may limit future improvements in spatial resolution of MRI measurement. Technological limitations include requirements for higher signal-to-noise ratio, more homogeneous and stable static magnetic field, and stronger and more linear magnetic field gradients. Physical limitations include the spectral signal line width and the effect of chemical shift on the measurement.

III. QMR (Quantitative Magnetic Resonance).

U.S. Pat. No. 5,270,651 issued to Wehrli discloses the use of the QMR method. This relaxometry-type method avoids the necessity for complicated and expensive equipment, but fails to overcome several limitations, such as trabecular bone being the only bone analyzed. As in the MRI method, fluids that occupy the intratrabecular spaces are not a simple type fluid, but include a mixture of blood, lipids, proteins and other fluids each having an individual NMR relaxation rate. Therefore, the NMR relaxation time spectrum may be extremely complicated, the relaxation time spectrum is also patient and skeletal site dependent, and the correlation between the relaxation time spectrum and the physical condition of bone, such as reduced BMD and consequent increase in risk of fractures (and more specifically osteoporotic conditions) is questionable. Internal magnetic field gradient distribution, which is the underlying phenomenon of this relaxometry QMR method, is not only a function of trabecular bone microstructure but also depends on the spatial distribution of the magnetic susceptibility of the materials being analyzed by NMR techniques. The assumption that the magnetic susceptibility of specific bone tissue and bone marrow is constant, as is required for this technique, is not highly accurate.

e. NMR techniques for analyzing materials other than human bone have been developed. These techniques, which are relevant to bone analysis, include the following:

NMR methods for quantitative analysis of moisture level or "solid" to "liquid" ratio are known in the art. Measuring fat content in margarine has become a very important application of such techniques. A more general approach is described, for example, in U.S. Pat. No. 5,539,309 issued to Van Wyk et al. which discloses a concept of "solid" to "liquid" ratio determination. Generally the technique works where there exist physically distinct phases having relaxation times which may be characterized as "fast" and "slow" relative to one another. This method is quite effective in cases when the relaxation times of the two phases are very different. The technique disclosed in the Van Wyk et al '309 patent, however, has low accuracy where the relaxation times are only marginally different, or when used for mixtures including several phases, such as for example, determining bound water content of fluid-bearing porous earth formations. Examples of similar applications includes: U.S. Pat. No. 5,818,228 issued to Menon et al. which discloses using a similar technique for measurement of the resin content of a composite material by NMR. U.S. Pat. No. 4,701,705 issued to Rollwitz which discloses a method for determining moisture of a material by determining the total hydrogen density of the material.

f. NMR technical issues relevant to NMR bone analysis include the following:

All of the previously described NMR techniques could be more effective if their signal-to-noise ratio could be improved significantly. This would lead to better precision, accuracy and spatial resolution irrespective of the selected NMR technique. This fact is recognized in an apparatus for noninvasive, localized, in-vivo examination of tissue, including bone, which is disclosed in U.S. Pat. No. 4,442,404 issued to Bergmann. The essence of the method and apparatus described in the Bergmann '404 patent is to use a detection coil maintained at superconducting temperature to achieve a high signal-to-noise ratio. This technique has not been used on a commercial basis due to engineering difficulties, and in many cases thermal noise is generated not only in the detection coil but also in the sample itself because the sample is electrically conductive.

Despite extensive research and development into methods of characterizing bone and the cause and treatment of osteoporosis, there is still a need for reliable, accurate, precise and specific non-invasive methods for acquiring information relating to the bone and for detecting, diagnosing and monitoring diseases such as osteoporosis.

SUMMARY OF THE INVENTION

One aspect of the invention is a method for analyzing a bone. The method includes measuring nuclear magnetic resonance (NMR) signals corresponding to an amount of hydrogen nuclei from within a selected portion of the bone, where the selected portion has a known volume. The signals measured from within the selected portion include components corresponding to bound water. Specific bone tissue volume is determined from an amplitude of the components corresponding to the bound water.

In one embodiment of this aspect of the invention, the NMR signals are measured using truncated Carr-Purcell-Meiboom-Gill (CPMG) pulse sequences. In this embodiment the amplitudes of the spin echoes measured are summed to determine the amplitude of the bound water components of the NMR signals. The CPMG pulse sequences are truncated by having a time between each pulse sequence which is shorter than the recovery time of the slower relaxing components in the bone.

Another aspect of the invention is a method for determining the collagen content of a bone. A bone mineral volume in a selected portion of the bone having a known volume is determined from the amplitude of the bound water components of the NMR signals. The fluid volume in the selected portion of the bone is also determined, from the NMR signals not related to the bound water. In one example, pulse sequences for measuring steady state free precession amplitudes are used to determine the total fluid volume in the selected portion of the bone. The collagen volume is determined as the difference between the total volume of the selected portion of the bone, and the fluid volume and bone mineral volumes thus determined.

Another aspect of the invention is a method for imaging a bone. The method of imaging includes inducing nuclear magnetic resonance within a selected discrete volume of the bone, determining an amplitude of components in signals detected from the induced nuclear magnetic resonance which are related to bound water in the bone, and repeating the inducing the magnetic resonance and determining the fast relaxing component amplitude at other selected discrete volumes within the bone to develop an image of the bone. In one embodiment of this aspect of the invention, the amplitudes of the bound water-related components are determined by measuring spin echo amplitudes of truncated CPMG sequences, where the sequences have wait times between them less than a relaxation time of the slower relaxing components in the bone, namely those not related to bound water.

In a particular embodiment of this aspect of the invention, the bone mineral content of each selected discrete volume is determined from the amplitude of the bound water signal components, and an image of the bone mineral content is developed from amplitudes measured within each of the selected discrete volumes.

DETAILED DESCRIPTION

Figure 1:
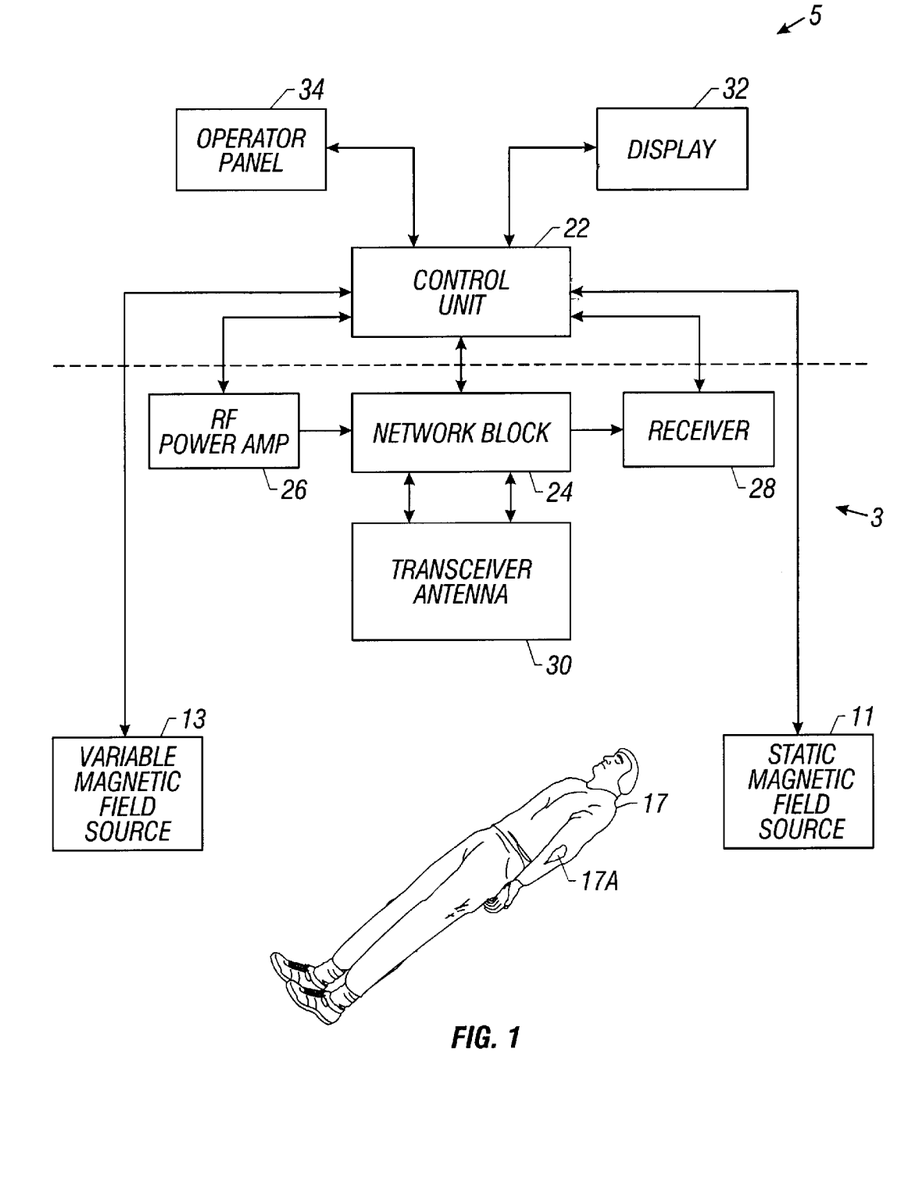
FIG. 1 shows one example of a nuclear magnetic resonance measuring system which can be used with the method of this invention.

FIG. 1 shows in general form one example of a nuclear magnetic resonance ("NMR") system used for bone analysis. The system includes a first portion 3, which is arranged to be located near a part 17 of a patient's body wherein is located a bone 17A that is to be examined by the system. The first portion 3 includes a static magnetic field source 11 which imparts a static magnetic field to the bone 17A. The static magnetic field source 11 may include one or more permanent magnets, conventional electromagnets or superconducting electromagnets or any combination thereof. The first portion 3 in this example also includes a variable magnetic field source 13, which may include one or more gradient coils connected to a gradient power source (not shown separately in FIG. 1) to induce variable gradient magnetic fields in the bone 17A. The term "static" as applied to the magnetic fields in this description means that the amplitude of the field does not vary in time, nor does the spatial distribution of the field vary during the NMR measuring cycle. The field amplitude of the static magnetic field, however, is not necessarily homogeneous in its spatial distribution. The term "variable" as used to describe magnetic fields herein means that the field amplitude is variable in space and/or in time during an NMR measuring cycle, but the variation occurs at rates which are much slower than radio frequencies ("RF") for which magnetic resonance condition are met for nuclei under investigation. In this example, the nuclei of interest are hydrogen nuclei. Both the source of the static magnetic field 11, if electromagnets are used, and the source of the variable magnetic field 13, can be powered and controlled by a control, processing, monitoring and safety unit (control unit) 22, which in this example is included in a second portion 5 of the system.

The first portion 3 also includes an RF magnetic field transceiver antenna 30. The RF magnetic field transceiver antenna (antenna) 30 can be interconnected to a network block 24. The network block 24 typically includes circuits (not shown separately in FIG. 1) such as a transceiver tuning circuit (which may itself include a series of resonance capacitors), a transmitter/receiver switch and both "to-transmitter" and "to-receiver" matching circuitry.

The network block 24 can be coupled both to an RF power amplifier 26 and to a receiver 28. While the network block 24, the RF power amplifier 26 and the receiver 28 are shown in FIG. 1 shown as being located inside the first part 3 of the system, it is to be understood that the whole network block 24, the RF power amplifier 26 and the receiver 28, or any part of these elements may be disposed partially or entirely within the second part 5 of the system. The particular locations of the network block 24, the RF power amplifier 26 and the receiver 28 or any parts of these elements are not to be construed as a limitation on the invention. The network block 24 in this example is controlled by the control unit 22, which in this example also controls the timing and operation of the RF power amplifier 26, and provides the receiver 28 with a phase reference and other coordination signals. In this example, the control unit 22 can also supply power to the RF power amplifier 26 and receiver 28. The RF power amplifier 26 provides a high power signal to drive the antenna 30 so as to generate an RF magnetic field in a selected discrete volume in the bone 17A which is to be examined by the system. The selected discrete volume will be further explained.

During reception of NMR signals from the bone being analyzed 17A, voltages are induced in the antenna 30. The output of the antenna 30 may be conducted via a preamplifier (not shown separately) to the receiver 28, and then to the control unit 22. Usually the preamplifier (not shown) forms part of the receiver 28, but preferably is positioned as closely as possible to the antenna 30 for signal processing reasons, and therefore in this example is considered part of the transceiver antenna 30.

The control unit 22, which in this example is operated through a separate operator panel 34 can include a computer (not shown separately) for processing the received NMR signals, and can transfer the processed signals and results of analysis thereof to a display 32 for presentation in any form which is useful to those skilled in the art of NMR measurements of bone properties.

Figure 2:
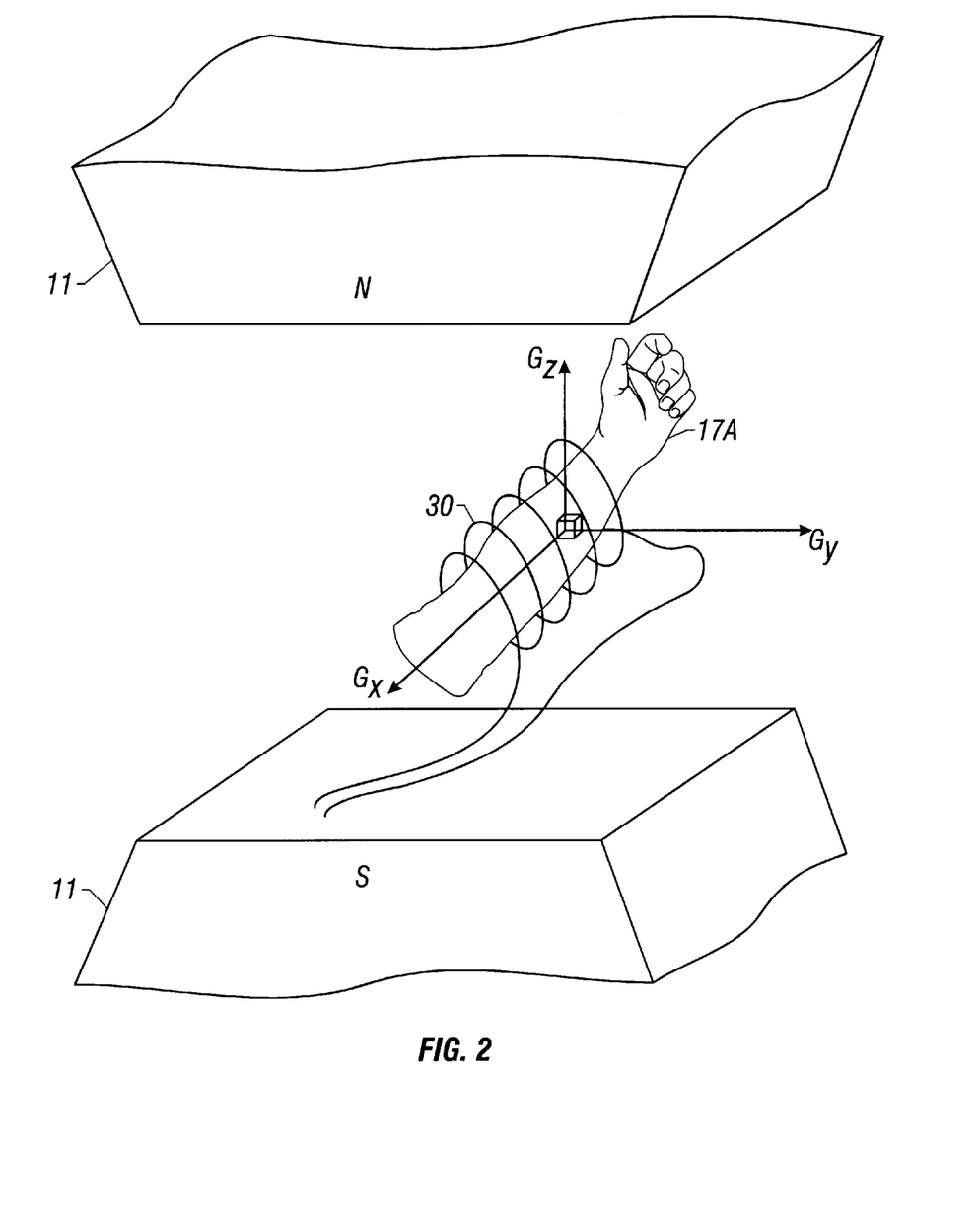
FIG. 2 shows in more detail a bone being analyzed using the system in FIG. 1.

FIG. 2 shows one embodiment of the antenna 30 and the static magnetic field source 11 in more detail. In this example, the static magnetic field source 11 is a permanent magnet arranged to induce a static magnetic field polarized normal to the longitudinal axis of the bone 17A (the bone axis being referred to as the x axis in FIG. 2), the polarization direction being along what is defined herein as the z axis. In this example, the bone 17A is the radius in the forearm, but as previously explained, the actual anatomical bone which is analyzed is not critical to the invention. The antenna 30 in this example is a coil wound so that its axis, and consequently the RF magnetic field it induces within the bone 17A, is substantially perpendicular to the static magnetic field imparted to the bone 17A by the magnet (the static field source 11). The antenna 30 in this example is a coil wound as shown in FIG. 2, but the antenna 30 may have any other convenient configuration which results in an RF magnetic field being induced in the bone 17A that is perpendicular to the static magnetic field within the selected discrete volume (which will be further explained).

Figure 3:
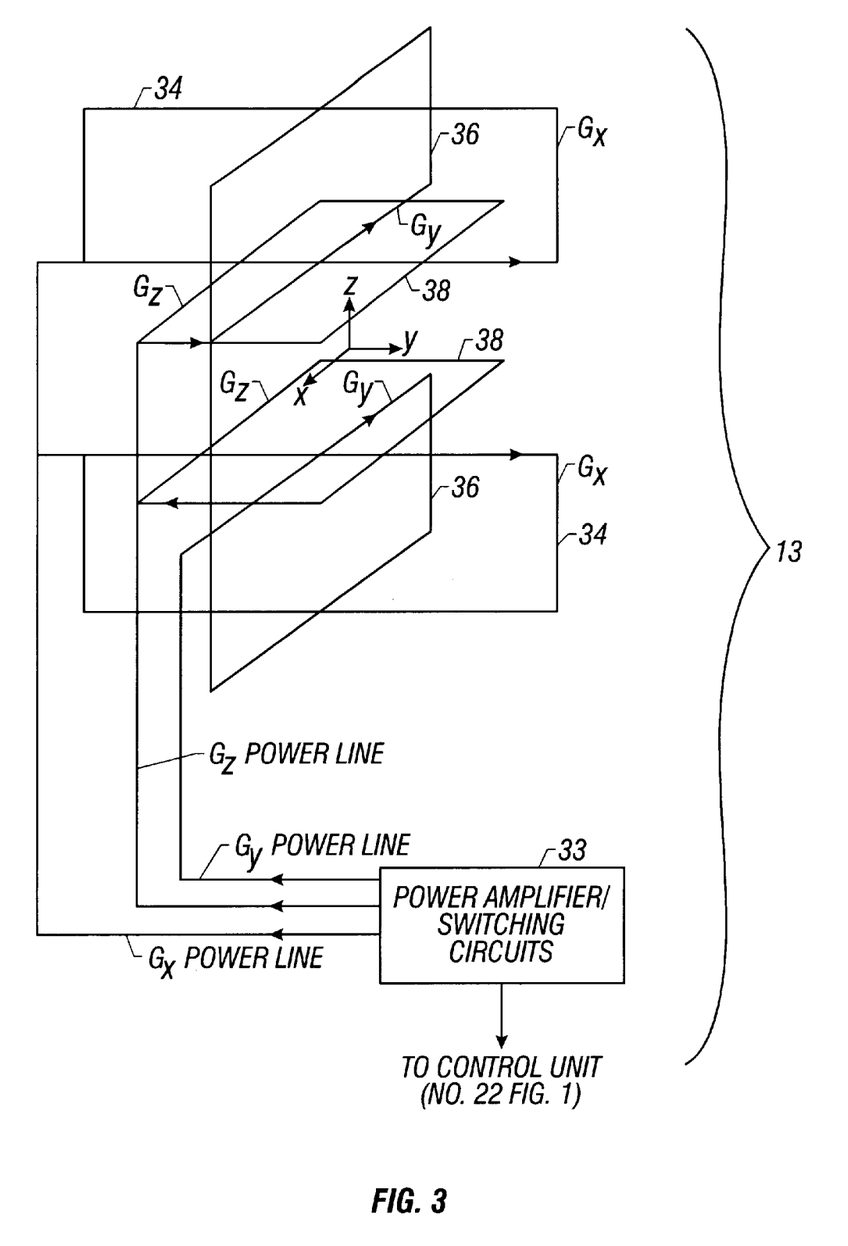
FIG. 3 shows an example of gradient coils used to localize NMR signals in the system of FIG. 1.

In this embodiment, gradients of the z component of the magnetic field are also induced in the bone 17A along mutually orthogonal axes, preferably x, y, and z axes as shown in FIG. 2 as $G_X$, $G_Y$ and $G_Z$. The purpose of these gradient magnetic fields is to localize the previously mentioned selected discrete volume, from which the NMR signal is detected in the transceiver antenna 30. FIG. 3 shows an example of gradient field coils which can be used to localize the NMR signal for purposes of the invention. The $G_X$ gradient is developed by passing current from a power amplifier/switching circuit 33 along $G_X$ power line to gradient coils 34. Corresponding connections can be made for $G_Y$ gradient coils 36 and $G_Z$ gradient coils 38. The current passed through the gradient coils 34, 36, 38 to localize the selected discrete volume is low frequency AC, the amplitude and frequency of which is selected so that only a selected, small, discrete volume in space between the gradient coils 34, 36, 38 has a substantially invariant amplitude static magnetic field therein. This discrete volume is the source of substantially all the NMR signal detected by the transceiver antenna (30 in FIG. 2). Localization of the NMR signal by applying alternating gradients is known in the art and is described, for example, in P. Mansfield and P. G. Morris, *NMR Imaging in Biomedicine*, p. 98, Academic Press, New York, 1982. The position in space of the discrete volume can be selected, for example, by applying appropriate amplitude bias gradients to the AC gradients, such as by applying unbalanced current in two coils with a separate power supply. Methods for selecting the position of the discrete volume are also well known in the art and are explained in the Mansfield and Morris reference, supra., for example.

The NMR signal being measured is related to the amplitude of voltages detected by the antenna (30 in FIG. 2). The signal amplitude, in turn, is related to the number of protons (hydrogen nuclei) disposed within the selected discrete volume and their relaxation time characteristics. One technique particularly suitable for the invention for measuring NMR-induced voltages related to proton numbers and relaxation time characteristics from within the selected discrete volume is known in the art as the Carr-Purcell-Meiboom-Gill (CPMG) pulse sequence. This technique includes passing an RF power pulse through the antenna (30 in FIG. 2) at the nuclear magnetic resonance frequency, where the RF power pulse has a duration sufficient to reorient the magnetic spin axes of the protons by about 90 degrees from alignment with the static magnetic field imposed by the source (11 in FIG. 2). The so-called "90 degree" RF pulse is followed after a selected time interval by a series of RF power pulses each having a duration selected to reorient the proton spin axes by about 180 degrees from their previous orientation. In the time between these successive so-called "180 degree" pulses, voltages are induced in the antenna (30 in FIG. 2). These voltages are related in amplitude to the magnitude of the component of the bulk nuclear magnetization which is along the sensitive axis of the antenna (30 in FIG. 2), and are referred to as "spin echoes". This technique, and variations of the CPMG technique, are well known in the art and are described in the Mansfield and Morris reference, supra, for example. The spin echo amplitudes have an initial magnitude, and decrease at rates which reflect certain physical properties of the material in the sensitive volume, including the number of excited nuclei within the sensitive volume, and the chemical nature of the excited nuclei. Other pulsing techniques are well known in the art and can also be used to determine numbers of hydrogen nuclei in the selected discrete volume, and relaxation time characteristics of these hydrogen nuclei.

In this aspect of the invention, the NMR signals from the excited hydrogen nuclei within the selected discrete volume are analyzed to determine particular properties of interest in the analyzed bone (17A in FIG. 1). It is desirable to localize the selected discrete volume within a known portion of the analyzed bone (17A in FIG. 1) so that the properties of the bone (17A in FIG. 1) determined from analysis of the NMR signals can be characterized according to a known quantity (usually length or volume) of the bone (17A in FIG. 1). Referring once again to FIG. 2, methods for localization will be explained. The magnet 11 in FIG. 2 has substantially zero amplitude gradient along the x axis where the antenna 30 is located. Alternating gradients can be applied through coils (such as 34, 36, 38 in FIG. 3) to produce a "slice" having a known thickness along the x axis in which the magnetic field amplitude is substantially invariant. The position, along the x axis, of the slice can be selected, for example, by application of appropriate bias gradients, as previously explained. Alternatively, the magnet 11 can be designed so that its magnetic field has a selected amplitude gradient along the x axis. The frequency of the RF pulses can be selected to excite magnetic resonance at a position along the x axis where the static magnetic field amplitude corresponds to the selected RF field frequency. The thickness of the "slice" along the x axis at the selected position will be related to the magnitude of the static magnetic field amplitude gradient and the bandwidth of the receiver (28 in FIG. 1). The total volume occupied by the selected discrete volume should be known, in any event.

The NMR signals are preferably measured using equipment and measurement techniques that have a dead time of no more than about 200 microseconds. The dead time can be minimized by techniques known in the art, such as using a relatively high amplitude static magnetic field, so that the NMR frequency is correspondingly high, and keeping the size of the transceiver antenna and any gradient coils to a minimum. Fully mineralized bone includes chemically bound hydrogen, and there are very small blood vessels and cavities in the bone, both of which induce NMR signals having a very short decay time spectrum. The NMR signals from these substances have typically been ignored in NMR techniques used to image parts of the body, primarily because of the relatively long system dead time of typical NMR imaging equipment. As a result, the significance of the short decay time signal components has previously gone unnoticed. By using equipment capable of measuring short decay time signals, the relative contribution of the bound water and other short decay-time signal components from the bone can be determined by any of several well known methods of relaxation time spectral analysis.

Figure 4:
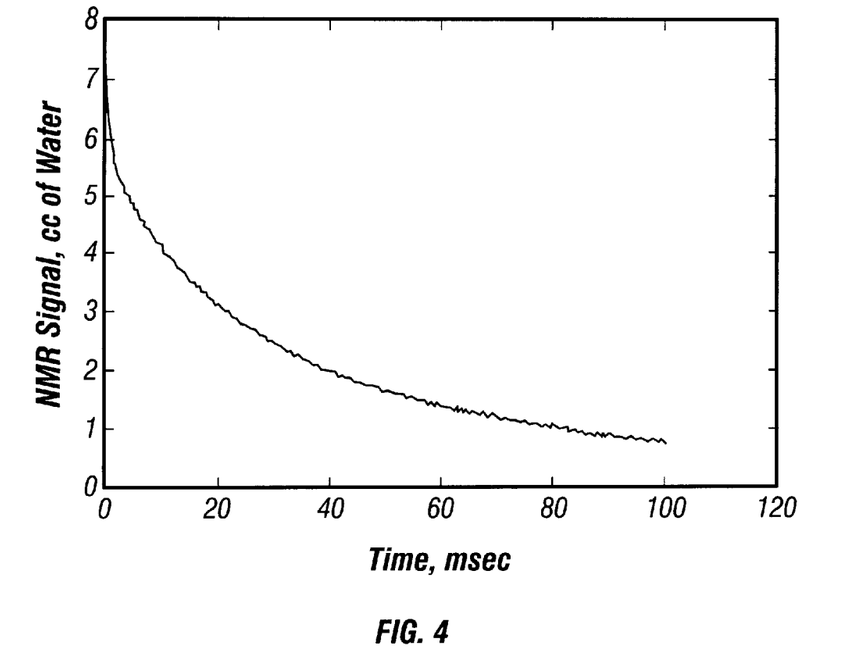
FIG. 4 shows a graph of spin echo magnitudes with respect to time measured by CPMG sequences of bone samples including cortical and cancellous bone.
Figure 5:
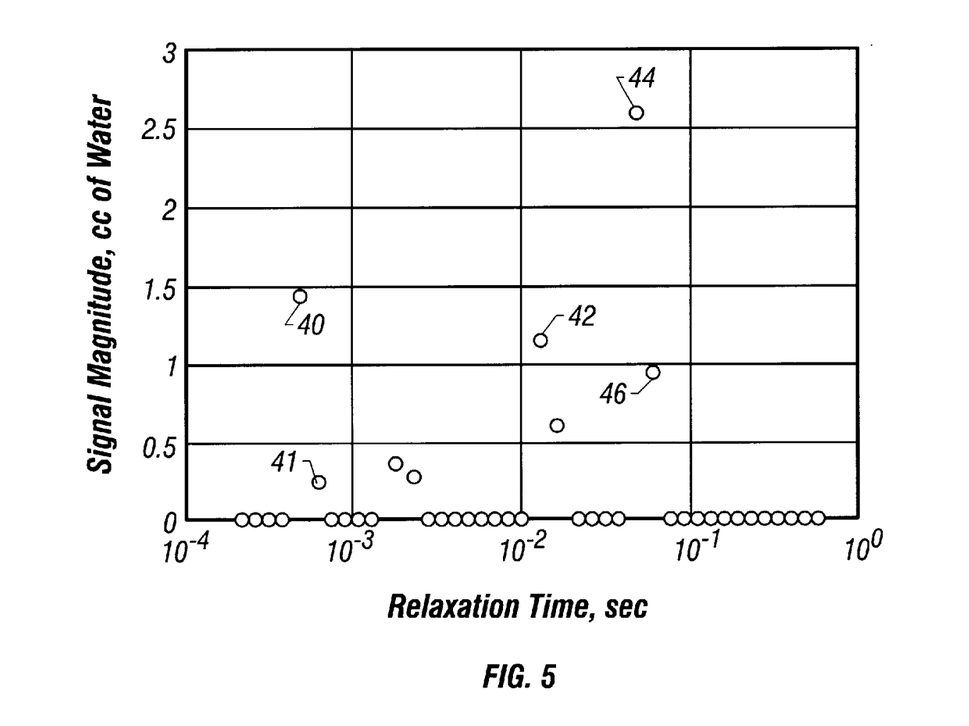
FIG. 5 shows a graph of relaxation time spectral analysis of the spin echo magnitudes shown in FIG. 4.
Figure 6:
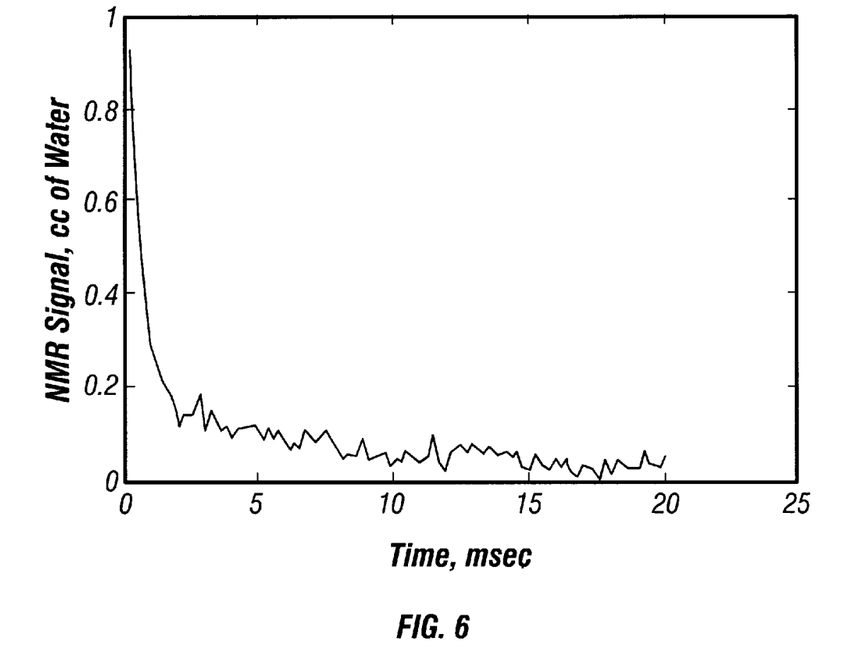
FIGS. 6 and 7 show, respectively, spin echo magnitudes and relaxation spectral analysis of NMR signals measured in cortical bone samples.
Figure 7:
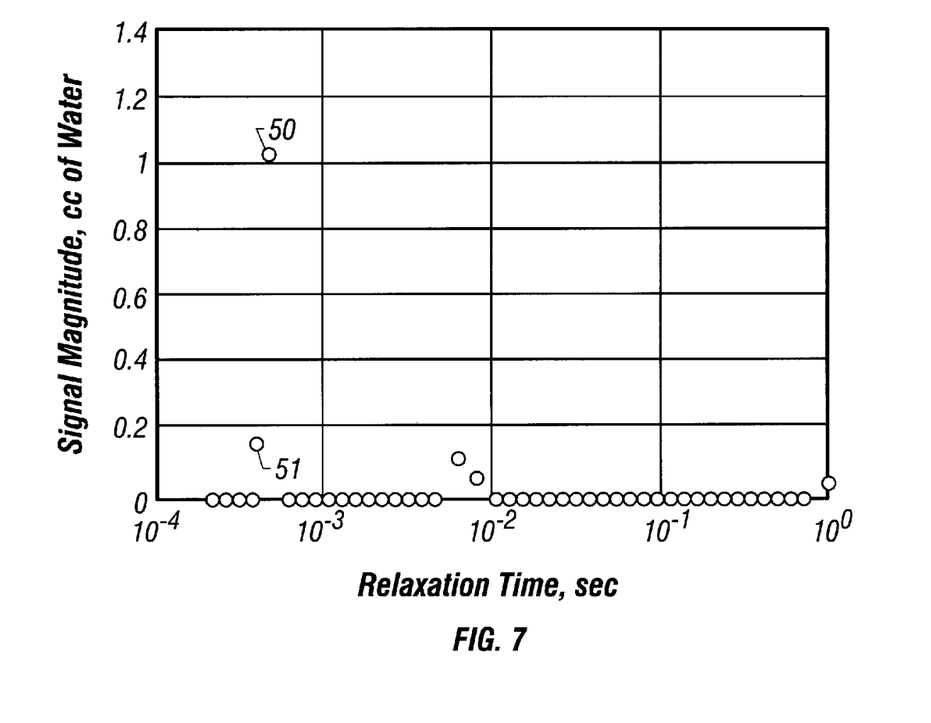

FIG. 4 shows a graph of magnitudes of spin echoes measured on bovine tibia samples. The bovine tibia samples included both cancellous (trabecular or "spongy") bone and cortical bone. Relaxation time spectral analysis of the spin echo magnitudes shown in FIG. 4 is shown in the graph in FIG. 5. A distinctive feature in the relaxation time spectral analysis shown in FIG. 5 is a component, shown at 40 and 41, having a specific relaxation time of about $5 \times 10^4$ seconds (500 microseconds). Other signal components having much longer specific relaxation times (more than 10 milliseconds) can also be observed on the graph in FIG. 5 at 42, 44, and 46. FIG. 6 shows a spin echo magnitude graph for bovine tibia samples consisting almost entirely of cortical bone. A relaxation time spectral analysis of the spin echo amplitudes of FIG. 6 is shown in the graph in FIG. 7. Of particular interest is that the component having specific decay time of about 500 microseconds, shown at 50 and 51, is also present in the NMR signals from the cortical bone sample. Notably absent from the spectral analysis in FIG. 7 are the signal components having relaxation times longer than about 10 milliseconds. This is consistent with the absence of substantial volumes of free (chemically not bound) fluid and/or fatty tissue within cortical bone.

Figure 8:
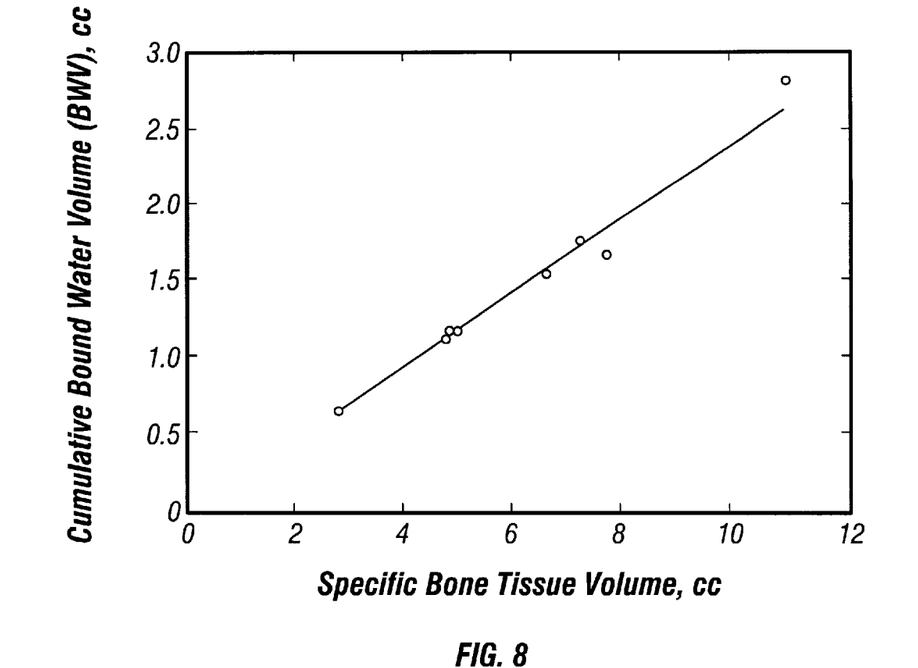
FIG. 8 shows a graph of the relationship between specific bone tissue volume and cumulative NMR signal magnitude for components having relaxation times less than about 1 millisecond for the samples analyzed as shown in FIGS. 4–7.

It has been determined through experimental analysis of the bovine tibia samples that the amplitude of the NMR signal component having relaxation time of about 500 microseconds corresponds very closely to the volume of specific bone tissue present in the sample. A graph showing this correspondence is shown in FIG. 8. The graph in FIG. 8 represents, on the ordinate axis, values directly related to the cumulative amplitude of the NMR signal components having relaxation time less than about 1 millisecond (1000 microseconds). These signals correspond to the bound water in the bone in these particular samples. The coordinate axis represents the difference between the total measured volume of the particular bone sample and the cumulative amplitude of all NMR signal components, having the more slowly relaxing components (those having relaxation times longer than about 1 millisecond). These signals correspond to fluids containing unbound hydrogen (so called "free fluid") in the bone. These fluids are not a part of the specific bone tissue in these particular samples. The difference represented on the ordinate axis of FIG. 8 corresponds directly to the volume of specific bone tissue in the sample volume. As can be observed in FIG. 8, there is very high correspondence between the amplitude of the fast-decaying NMR signal components and the specific bone tissue volume in the sample.

The relaxation time distribution in which mineralized bone provides NMR signal components having about 500 microseconds relaxation time has been demonstrated experimentally for bovine tibia. Other bones, and particularly human bones, may have other relaxation time components related to bound water present in the mineralized bone. The physical principle underlying the existence of short relaxation components in NMR signals will apply to any type of bone, however, since mineralized bone includes chemically bound water. Samples of the various types of bones which will be analyzed in vivo using an apparatus such as shown in FIG. 2, can be experimentally evaluated in vitro, for example from cadavers, to establish the relaxation time distributions thereof, and particularly the expected relaxation times of the bound water components therein. Relaxation time distributions can also be established in vivo by using apparatus such as shown in FIG. 2 programmed to measure extended CPMG pulse sequences, wherein the magnitude of free fluid components can also be determined.

Irrespective of the exact distribution of relaxation times in any particular bone or bone sample, the distribution of relaxation times will generally be bimodal. There will typically be a short relaxation time mode corresponding to chemically bound water, and a longer relaxation time mode corresponding to soft tissue, fat, blood, and water. Knowledge of the expected relaxation time distribution for the types of bones to be analyzed in vivo can be used to operate the apparatus shown in FIG. 2 with a more convenient, truncated CPMG sequence as will be further explained.

In practice, the analyzed bone (17A in FIG. 1) will have NMR measurements made within each of a plurality of selected slices (the discrete volumes) along the length of the analyzed bone (17A in FIG. 1). Specific bone tissue volume can be calculated, for each selected slice, by determining the amplitude of the NMR signal components having relaxation times less than the approximate upper time limit for bound water relaxation time components, determined for the particular bone as previously explained. Where the thickness of each of the selected slices is known, a profile of the bone (17A in FIG. 1) according to specific bone tissue content unit length of the bone (17A in FIG. 1) can be generated. It is contemplated that the procedure of analyzing a particular bone on a particular patient can be repeated at selected times to determine whether the specific bone tissue content per unit length has changed. Such profiling can aid physicians in diagnosis and monitoring of certain bone conditions characterized by changes in specific bone tissue content per unit volume or length of the bone.

In this example, the measurements made using the CPMG sequence correspond to the transverse relaxation time $T_2$ of the materials in the sensitive volume. It is clearly within the contemplation of this invention that measurements corresponding to the longitudinal relaxation time $T_1$ can also be used in the method of the invention. Pulse sequences for measuring $T_1$ are well known in the art.

As previously explained, prior knowledge of the expected upper limit of relaxation times of the so-called "fast decay" components in the NMR signals can be used to program an apparatus such as shown in FIG. 1 to measure spin echo amplitudes in truncated CPMG sequences. Such techniques are described, for example, in U.S. Pat. No. 5,596,274 issued to Sezginer. In the technique described in the Sezginer '274 patent, successive, truncated CPMG sequences having only a relatively limited number of spin echoes, approximately 10 to 50 echoes, are measured where the waiting time, TW, between each truncated CPMG sequence is selected to be less than the recovery time of nuclei whose contribution to the overall NMR signal measurement is not required. In the case of bone analysis, for example on bovine tibia, components having a relaxation time exceeding one millisecond can be excluded because such components are unrelated to the amount of bound water. Other bones, including human bones as previously explained, may have different exclusion or "cut off" times, which can be determined in vitro or in vivo as previously explained. By selecting a wait time, TW, shorter than the expected recovery times of the "slow relaxing" components, the slower relaxing nuclei are not able to realign themselves with the static magnetic field, and so are not excited to nuclear magnetic resonance in a manner which can be detected in a CPMG pulse sequence. In one example of this method, the amplitudes of all the spin echoes measured using short wait time CPMG sequences can be summed or stacked to improve the signal-to-noise ratio of the resulting measurement. Summing is suitable for this particular application because the fast decaying (bound water related) signal components herein have substantially only one value of relaxation time, and the quantity of interest is the signal amplitude or magnitude.

Figure 9:
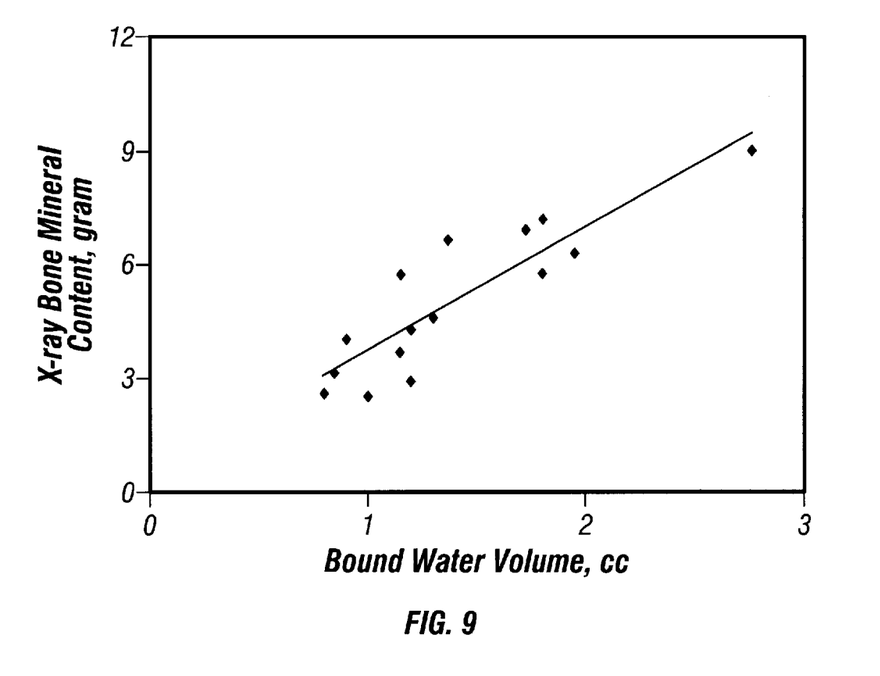
FIG. 9 shows a graph of the relationship between X-ray determined bone mineral content and the cumulative magnitude of the fast-relaxing NMR signal components for the samples analyzed as shown in FIGS. 4–7.

Another aspect of the invention includes a method for determining the volumetric and/or the mass fractions of collagen, bone mineral, and bound water within the specific bone tissue in the analyzed bone (17A in FIG. 2). As previously explained, the free fluid volume within the selected discrete volume or "slice" is related to the cumulative amplitude of the slower relaxing components of the NMR signal. The specific bone tissue volume is determined from the cumulative slow-relaxing signal component amplitude as the difference between the total volume of the selected discrete volume or "slice" and the free fluid volume determined from the slow relaxation component cumulative amplitude. In this example it is assumed that the bone mineral content is directly related to the cumulative amplitude of the fast-relaxing components. This assumption is based on the likelihood that bound water, from which the fast-relaxing signal components originate, is primarily associated with bone mineral and is not associated with collagen. Therefore, it is assumed that the bound water volume corresponds directly to the bone mineral content. A graph showing correspondence of bone mineral content, as determined by X-ray techniques (DXA in particular) and the cumulative amplitude of the fast relaxing components for the bovine tibia samples discussed earlier is shown in FIG. 9. Since the DXA technique, which was used in this set of experiments, is calibrated against ash weight (generally considered to be the bone mineral), the bone mineral content is equivalent to ash weight, and ash has a known density. Other types of bones, and human bones in particular, may have different correspondence between the bone mineral content (determined by DXA or ash weight) and the cumulative amplitude of the fast relaxing components, but the principle is the same in any case. Generally, the densities of the specific bone tissue and the bone mineral are known for a particular bone type and, therefore, all volumetric properties may be substituted by mass properties, and vice-versa.

Using the assumption that the bone mineral content is directly related to the fast-relaxing signal component amplitude, the amount of collagen can be determined as the difference between the total volume occupied by the slice or selected discrete volume, and the volumes of bone mineral and all fluids (free and bound) determined from the NMR measurements. In this embodiment of the invention, it is convenient to measure the total fluid volume by determining steady state free precession amplitudes of the hydrogen nuclei in the selected discrete volume. Methods for measuring steady state free precession amplitudes are described in the Mansfield and Morris reference, supra, for example. One example of this embodiment of the invention includes measuring bound water volume (and the bone mineral volume related thereto) by measuring amplitude from the previously described truncated CPMG sequences having short wait times between sequences, and measuring total fluid volume using steady state free precession amplitude pulse sequences.

Yet another aspect of the invention is a method for imaging bones using the bound water components of the NMR signal to develop image pixels. In general, magnetic resonance imaging is a relatively slow process because of the long waiting time needed between pulse sequences for the slowly relaxing materials being imaged to recover after each pulse sequence. Typically the measurement pulse sequence must be repeated for each image pixel. By using pulse sequences adapted to measure only the faster relaxing components (bound water related components) in developing an image, the process can be considerably speeded. The discrete volume, selected and positioned by methods explained earlier herein for example, can be reduced in size by, among other methods, selection of appropriate oscillating gradient amplitudes and frequencies, or selection of appropriate static field gradients and receiver bandwidths. Truncated CPMG sequences as described earlier herein can be measured in a plurality of such reduced size discrete volumes, where the reduced size discrete volumes are spatially distributed to cover a bone or part thereof being imaged. An image, using any suitable image developing technique known in the art, can be developed from the amplitude of the fast relaxing (bound water) components as measured in each such reduced size selected discrete volume within the bone or part thereof being imaged. The image pixel magnitude, brightness or density can be calibrated to the bone mineral content or bone matrix content determined from the amplitude of the fast-relaxing signal components determined as previously explained in addition to calibration to the amplitude. By calibrating pixel density to the bone mineral or matrix content, an image of either property can be developed directly.

As will be appreciated by those skilled in the art, slower relaxing materials, such as the soft tissues adjacent to the bone being imaged, will have substantially zero signal amplitude (appear black) because they have substantially no bound water. However, the image technique described herein is intended to image the internal structure of the bone itself, rather than the external shape of the bone. This artifact of the present technique therefore should not be objectionable. Because the bound water-related signals can be measured using truncated pulse sequences, the technique for imaging bones in this aspect of the invention provides more rapid, higher signal to noise imaging than prior art imaging techniques which measure NMR signals primarily related to the slower relaxing materials in the image volume.

It will be apparent to those skilled in the art that the embodiments of the invention described herein are only examples of the invention. Other embodiments of the invention can be developed which do not depart from the spirit of the invention as described herein. Accordingly, the invention should be limited in scope only by the attached claims.

What is claimed is:

1. A method for analyzing a bone, comprising:
   measuring nuclear magnetic resonance signals corresponding to a number of hydrogen nuclei from within a selected portion of said bone, said selected portion having a known volume, said measured signals including components corresponding to bound water; and
   determining a specific bone tissue volume of said selected portion of said bone from an amplitude of said bound water signal components.

2. The method as defined in claim 1 wherein said nuclear magnetic resonance signals comprise CPMG spin echo amplitudes.

3. The method as defined in claim 1 wherein a system used to measure said nuclear magnetic resonance signals has a dead time of less than about 200 microseconds.

4. The method as defined in claim 1 wherein said selected portion of said bone is determined by:
   applying a static magnetic field to said bone having substantially zero amplitude gradient along a selected direction; and
   superimposing oscillating gradient magnetic fields to said static magnetic field so that a combined magnetic field applied to said bone has substantially invariant amplitude only within said selected portion.

5. The method as defined in claim 4 wherein said selected portion is selectively moved along said selected direction by superimposing selected bias gradient magnetic fields to said oscillating gradient magnetic fields.

6. The method as defined in claim 1 wherein said selected portion of said bone is determined by:
   applying a static magnetic field to said bone having a predetermined amplitude gradient along a selected direction; and
   selecting a frequency for a radio frequency magnetic field used to excite nuclear magnetic resonance which matches resonance conditions of an extant total magnetic field at a selected position along said selected direction.

7. The method as defined in claim 6 wherein a thickness of said selected portion is determined by selecting a magnitude of said amplitude gradient and a bandwidth of a receiver used to detect said nuclear magnetic resonance signals which result in a predetermined thickness in said selected portion.

8. The method as defined in claim 1 further comprising determining a collagen volume of said selected portion of said bone by determining a fluid volume in said selected portion from said nuclear magnetic resonance signals corresponding to unbound hydrogen, and subtracting from said known volume of said selected portion said fluid volume and a bone mineral content determined from said amplitude of said signal components corresponding to bound water.

9. The method as defined in claim 8 wherein said amplitude of said bound water components is determined by measuring truncated CPMG sequences, said truncated sequences having wait times therebetween shorter than a recovery time of components other than said bound water present in said bone, and said signals corresponding to unbound hydrogen are determined by measuring a steady state free precession amplitude within said selected portion of said bone.

10. The method as defined in claim 8 further comprising repeating said measuring, determining said bone mineral content and determining said collagen volume at selected time intervals to determine changes in said bone mineral content and said collagen volume corresponding to diseases of said bone.

11. The method as defined in claim 1 further comprising repeating said measuring and determining said specific bone tissue volume at selected time intervals to determine changes in said specific bone tissue volume corresponding to diseases of said bone.

12. The method as defined in claim 1 wherein said amplitude of said bound water components is determined by measuring truncated CPMG sequences, said truncated sequences having wait times therebetween shorter than a recovery time of longer relaxing components within said bone.

13. A method for magnetic resonance imaging of a bone, comprising:
   inducing nuclear magnetic resonance within a selected discrete volume of said bone;
   determining an amplitude of components related to bound water in signals detected from said induced nuclear magnetic resonance; and
   repeating said inducing and determining said amplitude at other selected discrete volumes within said bone to develop an image of said bone.

14. The method as defined in claim 13 further comprising:
   calculating a bone mineral content within said selected discrete volume of said bone and said other selected discrete volumes from said amplitudes of said components corresponding to bound water; and
   developing an image of said bone based on said bone mineral content determined at said selected discrete volume and said other selected discrete volumes.

15. The method as defined in claim 13 further comprising:
calculating specific bone content within a selected discrete volume of said bone and said other selected discrete volumes from said amplitude of said signals corresponding to bound water; and
developing an image based on said specific bone content determined at said selected discrete volume and said other selected discrete volumes.

16. The method as defined in claim 13 further comprising:
calculating collagen content within a selected discrete volume and said other selected discrete volumes of said bone from said amplitude of said signals corresponding to bound water; and
developing an image of said bone based on said calculated collagen content in said selected discrete volume and said other selected discrete volumes.

17. The method as defined in claim 13 wherein said amplitude is determined by measuring truncated CPMG sequences, said truncated sequences having wait times therebetween shorter than a recovery time of longer relaxing components within said bone.

18. A method for analyzing a bone, comprising:
measuring nuclear magnetic resonance signals corresponding to a number of hydrogen nuclei from within a selected portion of said bone, said selected portion having a known volume, said measured signals including components corresponding to bound water; and
determining a bone mineral content of said selected portion of said bone from an amplitude of said bound water signal components.

19. The method as defined in claim 18 further comprising determining a collagen volume of said selected portion of said bone by determining a fluid volume in said selected portion from components of said nuclear magnetic resonance signals corresponding to unbound hydrogen, and subtracting from said known volume of said selected portion said fluid volume and a bone mineral volume determined from said bone mineral content determined from said signal components corresponding to bound water.

20. The method as defined in claim 19 wherein said amplitude of said bound water components is determined by measuring truncated CPMG sequences, said truncated sequences having wait times therebetween shorter than a recovery time of components other than said bound water present in said bone, and said signals corresponding to unbound hydrogen are determined by measuring a steady state free precession amplitude within said selected portion of said bone.

21. The method as defined in claim 19 further comprising repeating said measuring, determining said bone mineral volume and determining said collagen volume at selected time intervals to determine changes in said bone mineral volume and said collagen volume corresponding to diseases of said bone.

22. The method as defined in claim 19 further comprising repeating said measuring and determining said specific bone tissue volume at selected time intervals to determine changes in said specific bone tissue volume corresponding to diseases of said bone.

23. The method as defined in claim 19 wherein said amplitude of said bound water components is determined by measuring truncated CPMG sequences, said truncated sequences having wait times therebetween shorter than a recovery time of longer relaxing components within said bone.

* * * * *